United States Patent
Wager

(10) Patent No.: US 7,885,823 B2
(45) Date of Patent: Feb. 8, 2011

(54) COMPUTERIZED SYSTEM AND METHOD FOR MANAGING PERSONNEL DATA IN A HEALTHCARE ENVIRONMENT

(75) Inventor: Doug Wager, Kansas City, MO (US)

(73) Assignee: Cerner Innovation, Inc., Overland Park, KS (US)

( * ) Notice: Subject to any disclaimer, the term of this patent is extended or adjusted under 35 U.S.C. 154(b) by 1566 days.

(21) Appl. No.: 11/027,369

(22) Filed: Dec. 30, 2004

(65) Prior Publication Data

US 2006/0149593 A1 Jul. 6, 2006

(51) Int. Cl.
*G06Q 50/00* (2006.01)
(52) U.S. Cl. .............................. 705/2; 600/300; 705/3; 705/10; 702/182
(58) Field of Classification Search ................. 705/2–3, 705/10; 600/300; 702/182
See application file for complete search history.

(56) References Cited

U.S. PATENT DOCUMENTS

| | | | |
|---|---|---|---|
| 5,324,077 A | | 6/1994 | Kessler et al. |
| 5,583,758 A | | 12/1996 | McIlroy et al. |
| 5,953,704 A | | 9/1999 | McIlroy et al. |
| 6,151,581 A | * | 11/2000 | Kraftson et al. ............. 705/3 |
| 7,529,682 B2 | | 5/2009 | Geller et al. |
| 2002/0059080 A1 | * | 5/2002 | Kasirer et al. ............... 705/2 |
| 2003/0036921 A1 | * | 2/2003 | Ito et al. ...................... 705/1 |
| 2003/0167187 A1 | * | 9/2003 | Bua .............................. 705/2 |
| 2003/0236682 A1 | | 12/2003 | Heyer |
| 2004/0039603 A1 | * | 2/2004 | Hanrahan .................... 705/2 |
| 2004/0117617 A1 | | 6/2004 | Geller |
| 2006/0053035 A1 | | 3/2006 | Eisenberg |
| 2006/0149592 A1 | | 7/2006 | Wager et al. |

OTHER PUBLICATIONS

American DataBank, http://www.americandatabank.com/healthcare.asp p. 1-15.*
American DataBank, Jun. 18, 2003, http://www.americandatabank.com/healthcare.asp p. 1-15.*

* cited by examiner

*Primary Examiner*—Gerald J. O'Connor
*Assistant Examiner*—Sind Phongsvirajati
(74) *Attorney, Agent, or Firm*—Shook Hardy & Bacon LLP

(57) ABSTRACT

The invention relates to a system and method in a computing environment for managing healthcare personnel data elements for at least one healthcare professional. In accordance with one method of the invention, first and second healthcare personnel data elements for a healthcare professional are received from first and second primary source providers. The first and second healthcare personnel data elements are associated with a profile for the healthcare professional. The profile is a repository for numerous pieces of healthcare personnel data elements for the healthcare professional and may be continuously updated with current healthcare personnel data elements. The first and second healthcare personnel data elements are stored with the profile for the healthcare professional.

12 Claims, 5 Drawing Sheets

COMPUTERIZED SYSTEM AND METHOD FOR MANAGING PERSONNEL DATA IN A HEALTHCARE ENVIRONMENT

CROSS-REFERENCE TO RELATED APPLICATIONS

This application is related by subject matter to the invention disclosed in the commonly assigned application U.S. application Ser. No. 11/027,367, filed on even date herewith, entitled "COMPUTERIZED SYSTEM AND METHOD FOR PROVIDING PERSONNEL DATA NOTIFICATIONS IN A HEALTHCARE ENVIRONMENT."

STATEMENT REGARDING FEDERALLY SPONSORED RESEARCH OR DEVELOPMENT

Not applicable.

TECHNICAL FIELD

The present invention relates to the field of computer software. More specifically, the present invention also relates to a system and method for collecting and distributing personnel information in a healthcare environment.

BACKGROUND OF THE INVENTION

Healthcare providing organizations, such as hospitals and physician offices, often must verify information regarding healthcare professionals, such as physicians and nurses, for a number of purposes, such as regulatory compliance and determining whether to employ or contract with the healthcare professional. These organizations may also wish to know information relating to the healthcare professional's practice history and qualifications. In addition, healthcare providing organizations must obtain claim information for every privileged or employed medical staff member every two years and maintain these records. Other healthcare related organizations, such as payors and malpractice insurance providers, also need verified healthcare personnel data for making business decisions and complying with regulatory requirements. However, the current process of obtaining and verifying healthcare personnel data is tedious and difficult.

There are no simple systems for consistent and automated data collection from a variety of primary sources of healthcare personnel data that can be shared electronically with appropriate consumers of that data. Instead, a variety of different organizations are managing and maintaining different pieces of the same information about healthcare professionals in different places. This makes consistency and accuracy of data more difficult, and takes more time to manage the information. Organizations end up verifying the same data multiple times, causing waste and inefficiency in the verification process, and introducing greater opportunity for error. In addition, many primary source providers do not have sophisticated technologies for managing and communicating data, nor do they have resources to develop such technology.

Credential verification organizations offer services to gather and provide information for individual healthcare professionals. However, these organizations must contact each primary source provider of data for each individual request to obtain the information and ensure that it is verified and accurate. Moreover, these services only provide a static snapshot of the healthcare professional's information. The data provided is only the currently available information and is not maintained and updated as information regarding the healthcare professional changes. Further, the services fail to capture a variety of other important information, such as treatment outcome data.

The National Practitioner Data Bank (NPDB) and Healthcare Integrity and Protection Bank (HIPDB) capture claims against healthcare professionals made by the government, organizations, or individuals. However, this information in and of itself doesn't provide insight to the quality of the healthcare professional. Only negative incidences are contributed to the data bank, and there is no ability to look at the outcomes of the professional's practice with respect to other professionals providing similar services.

Accordingly, what is needed is a system that provides a comprehensive, integrated healthcare personnel record at a single repository. Additionally, it would be desirable for such a system to allow for the automated, electronic collection and distribution of healthcare personnel data among a wide variety of entities.

SUMMARY OF THE INVENTION

In some embodiments, the invention relates to a system and method in a computing environment for managing healthcare personnel data for at least one healthcare professional. Thus, in one aspect, an embodiment of the present invention relates to a method in a computing environment for managing healthcare personnel data elements for a healthcare professional. A first healthcare personnel data element for a healthcare professional is received from a first primary source provider. A second healthcare personnel data element for the healthcare professional is received from a second primary source provider. The received first and second healthcare personnel data elements are associated with a profile for the healthcare professional. The profile is a repository for a number of healthcare personnel data elements for the healthcare professional and may be continuously updated with current healthcare personnel data elements. The received first and second healthcare personnel data elements are stored in the profile.

In another aspect of the invention, an exemplary embodiment is directed to a computerized system for managing healthcare personnel data for a healthcare professional. The system includes a receive component, an associating component, and a storage component. The receiving component receives a first healthcare personnel data element for a healthcare professional from a first primary source provider and a second healthcare personnel data element for the healthcare professional from a second primary source provider. The associating component associates the first and second healthcare personnel data elements with a profile for the healthcare professional. The profile is a repository for a plurality of healthcare personnel data elements for the healthcare professional and may be continuously updated with current healthcare personnel data elements. The storage component stores the first and second healthcare personnel data elements in the profile.

In yet another aspect, an exemplary embodiment of the invention takes the form of a system for managing healthcare personnel data. The system includes a network, a plurality of primary source providers, and a personnel profile manager. The plurality of primary source providers provide healthcare personnel data for at least one healthcare professional. The personnel profile manager communicates with the plurality of primary source providers via the network to receive and store the healthcare personnel data for the at least one healthcare professional.

In still a further aspect of the invention, an exemplary embodiment relates to a method for managing healthcare personnel data for a healthcare professional. A first healthcare personnel data element for a healthcare professional is received from an entity. The first healthcare personnel data element is associated with and stored in a profile for the healthcare professional. A request is received for a second healthcare personnel data element for the healthcare professional from the entity. The requested second healthcare personnel data element is sent to the entity.

BRIEF DESCRIPTION OF THE DRAWINGS

The present invention is described below in detail with reference to the attached drawing figures, wherein.

DETAILED DESCRIPTION OF THE INVENTION

Figure 1:
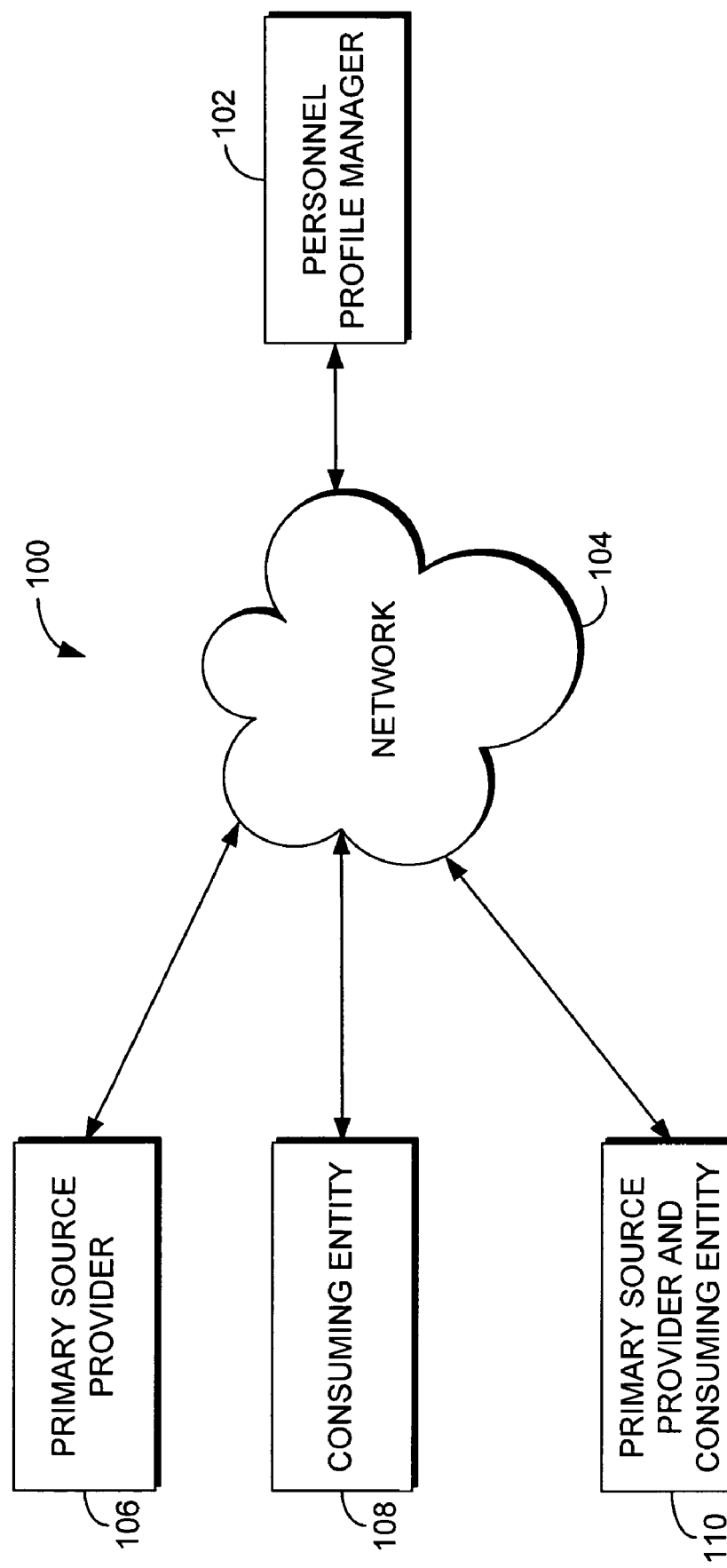
FIG. 1 is a block diagram of a computing system environment of an embodiment of the present invention.

The present invention may be implemented in a variety of computing system environments. For example, the invention may be embodied in an application program running on one or more personal computers (PCs). This computing system environment is only one example of a suitable computing environment and is not intended to suggest any limitation as to the scope of use or functionality of the invention. The invention may also be implemented with numerous other general purpose or special purpose computing system environments or configurations. Examples of other well-known computing systems, environments, and/or configurations that may be suitable for use with the invention include, but are not limited to, server computers, hand-held or laptop devices, multiprocessor systems, microprocessor-based systems, programmable consumer electronics, network PCs, minicomputers, mainframe computers, distributed computing environments that include any of the above systems or devices, and the like.

The invention may be described in the general context of computer-executable instructions, such as program modules. Generally, program modules include routines, programs, objects, components, segments, schemas, data structures, etc. that perform particular tasks or implement particular abstract data types. The invention may also be practiced in distributed computing environments where tasks are performed by remote processing devices that are linked through a communications network. In a distributed computing environment, program modules may be located in both local and remote computer storage media including memory storage devices.

Computers typically include a variety of computer-readable media. Computer-readable media includes any media that can be accessed by a computer and includes both volatile and nonvolatile media, removable and non-removable media. By way of example, and not limitation, computer-readable media may comprise computer storage media and communications media. Computer storage media include both volatile and nonvolatile, removable and non-removable media implemented in any method or technology for storage of information such as computer-readable instructions, data structures, program modules or other data. Computer storage media includes, but is not limited to, RAM, ROM, EEPROM, flash memory or other memory technology, CD-ROM, digital versatile disks (DVD), holographic or other optical storage, magnetic cassettes, magnetic tape, magnetic disk storage or other magnetic storage devices, or any other medium which can be used to store the desired information and which can be accessed by a computer.

Communications media typically embodies computer-readable instructions, data structures, program modules or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communications media includes wired media such as a wired network or direct wired connection, and wireless media such as acoustic, RF, infrared, spread spectrum and other wireless media. Communications media are commonly used to upload and download information in a network environment, such as the Internet. Combinations of any of the above should also be included within the scope of computer-readable media.

The computer may operate in a networked environment using logical connections to one or more remote computers, such as a personal computer, a server, a router, a network PC, a peer device or other common network node, and typically includes many or all of the elements described above. The logical connections may include connections to a local area network (LAN), a wide area network (WAN) and/or other networks. Such networking environments are commonplace in offices, enterprise-wide computer networks, intranets and the Internet.

Computer storage mechanisms and associated media provide storage of computer-readable instructions, data structures, program modules and other data for the computer. A user may enter commands and information into the computer through input devices such as a keyboard and pointing device, commonly referred to as a mouse, trackball or touch pad. Other input devices may include a microphone, touchscreen, camera, joystick, game pad, scanner, or the like. In addition to a monitor or other type of display device, computers may also include other peripheral output devices such as speakers and printers, which may be connected through an output peripheral interface.

Although many other internal components of computers have not been discussed herein, those of ordinary skill in the art will appreciate that such components and their interconnection are well-known. Accordingly, additional details concerning the internal construction of computers need not be disclosed in connection with the present invention.

The invention provides a system and method for managing healthcare personnel data by providing a single repository of information about healthcare professionals from various sources. A healthcare professional may be a physician, nurse, or generally any person who provides healthcare services to patients. The healthcare personnel data maintained by the system define aspects of a healthcare professional that may be needed for business decisions and regulatory compliance. The data relate to the qualifications, credentials, and capabilities of a healthcare professional to perform a certain healthcare related job and may include information such as degrees, licensing, certifications, malpractice insurance, and quality indicators.

With reference to FIG. 1, a block diagram of an exemplary embodiment of the invention is provided that illustrates a system 100 for managing healthcare personnel data. The system is a continuously updated, end-to-end process supported by computer modules that help entities distribute and obtain information regarding healthcare personnel. The invention includes a personnel profile manager 102, which provides a single location for collecting and distributing information regarding healthcare professionals.

Personnel profile manager 102 may be updated with healthcare personnel data and may distribute the data via network 104. Network 104 may include one or more wide area networks (WANs) and/or one or more local area networks (LANs), as well as one or more public networks, such as the Internet, and/or one or more private networks.

Primary source providers (PSPs), such as primary source provider 106, serve as the source of information regarding healthcare professionals. System 100 provides appropriate data management and review tools to each of the PSPs. The system may also interface with existing PSP systems where optimal to retrieve existing data. Thus, information maintained by the personnel profile manager may be continuously updated by PSPs as changes in healthcare personnel data occur. Data that are collected and maintained by the personnel profile manager 102 may be requested and provided to consuming entities, such as consuming entity 108. As depicted by primary source provider and consuming entity 110, some entities may serve as both providers and consumers of healthcare personnel data.

Figure 2:
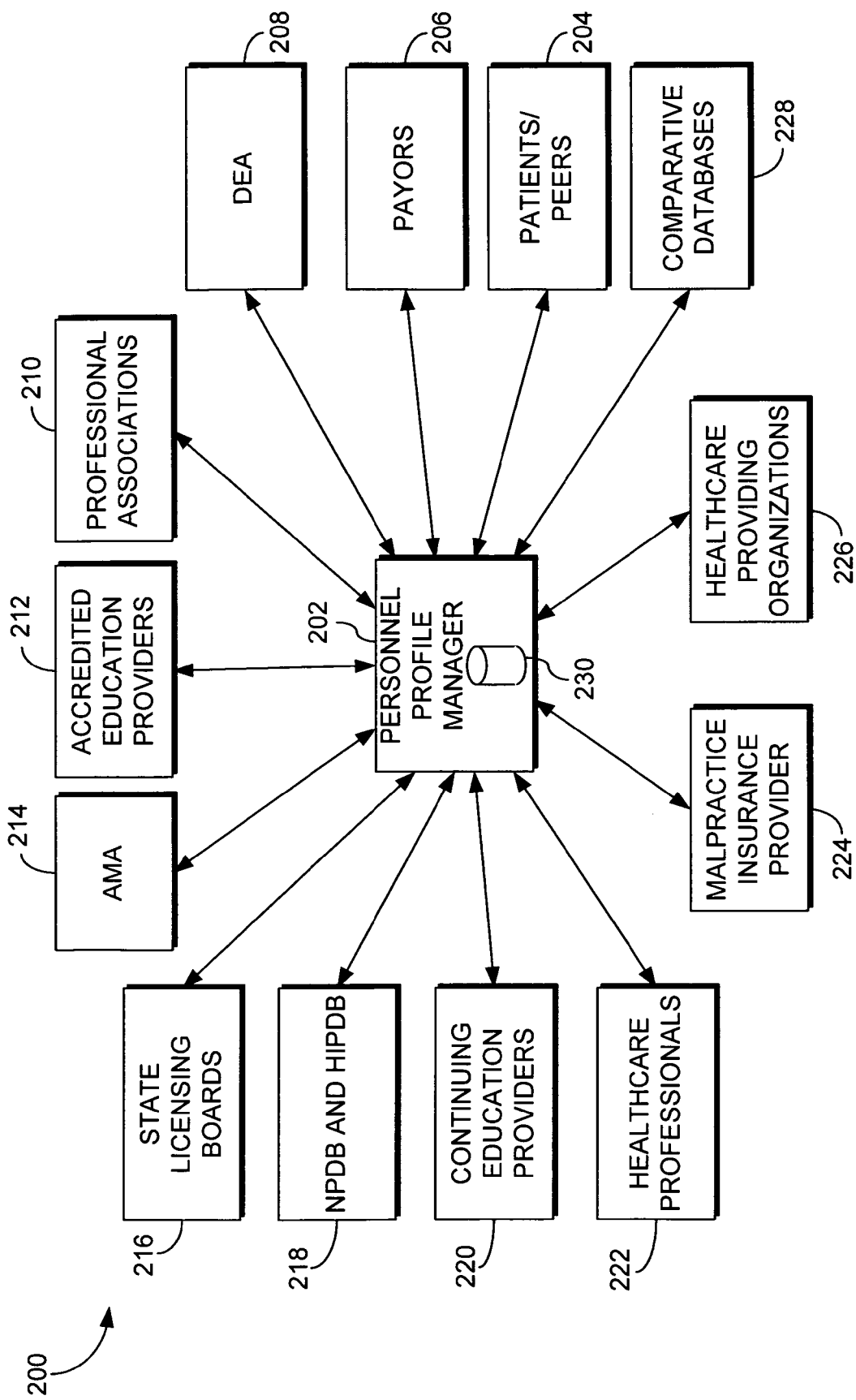
FIG. 2 is a block diagram of a computing system environment showing primary source providers and consuming entities in accordance with an embodiment of the present invention.

A more detailed block diagram illustrating an exemplary embodiment of a system for managing healthcare personnel data 200 is shown in FIG. 2. The diagram illustrates a number of PSPs that may provide healthcare personnel data to personnel profile manager 202, as well as consuming entities that may request the data. The diagram is intended to be an exemplary depiction of PSPs and consuming entities that may be a part of the system. Other PSPs and consuming entities that are not shown may be included within the scope of the invention. In addition, PSPs and consuming entities depicted in the diagram may be excluded.

As shown in FIG. 2, PSPs and consuming entities may include patients/peers 204, payors 206, the United States Drug Enforcement Administration (DEA) 208, professional associations 210, accredited education providers 212, the American Medical Association (AMA) 214, state license board systems 216, the National Practitioner Data Bank (NPDB) and Healthcare Integrity Protection Data Bank (HIPDB) 218, continuing education providers 220, healthcare professionals 222, malpractice insurance providers 224, healthcare providing organizations 226, and comparative databases 228. Although the following description may discuss each of these entities in only one role, each of the entities may serve as both a PSP and a consuming entity. Further, each of the entities may provide and consume data in addition to the data discussed below.

Patients/peers 204 may be one source of healthcare personnel data provided to the personnel profile manager 202. Hospitals often perform peer polling or reviews of their contracted/employed healthcare professionals and maintain the reviews as a part of their records. In addition, patients may be requested to provide a rating of services with respect to the healthcare professionals treating them.

Payors 206 may serve as both a PSP and a consuming entity. Data provided by payors may include information regarding the plan memberships held by healthcare professionals. Payors 206 may also consume a variety of information provided by other entities, such as physician credentialing data and quality indicators, in determining whether to provide plan memberships to healthcare professionals.

All physicians who wish to prescribe controlled substances must acquire a registration number from the DEA 208. In addition, all prescriptions from a physician must include that physician's DEA number. Thus, the DEA 208 may serve as source of information by providing DEA numbers for physicians to the personnel profile manager 202.

Professional associations 210 may serve as both PSPs and consuming entities. Data provided by the professional associations 210 may include certification by or membership in particular associations. Many professional associations 210 often require professionals to periodically provide information to be re-certified or to maintain their certification or registration. For example, some healthcare professionals may be required to have a certain number of practice hours to maintain their certification. Thus, professional associations 210 may serve as consuming entities of any information required for maintaining certifications and registrations.

Accredited education providers 212 include universities having accredited degree programs for healthcare professionals. These entities may provide information relating to degrees earned by healthcare professionals.

The AMA 214 tracks licenses held by physicians. Thus, the AMA 214 may serve as a PSP for physician licensing data. State licensing boards 216 also maintain information regarding physician licensing, as well as licensing for other healthcare professionals, such as nurses. In addition to being a PSP of licensing information, state licensing boards 216 may serve as consuming entities by requesting healthcare personnel data, such as continuing education courses taken, for purposes of license applications and license renewals.

The NPDB and HIPDB 218 capture information regarding claims against healthcare providers made by the government, organizations, or individuals. The databanks also maintain information relating to reported sanctions placed on healthcare professionals. Thus, the databanks may serve as PSPs of this information.

Continuing education providers 220 may serve as PSPs of continuing education courses taken by healthcare professionals. Alternatively, this information may be self-reported by individual healthcare professionals. Thus, healthcare professionals 222 may also serve as PSPs of data. In addition to continuing education courses taken, healthcare professionals 222 may provide other self-reporting data, such as contact information.

Malpractice insurance providers 224 may serve as PSPs of malpractice insurance related information, such as the policy ID number for individual healthcare professionals. This data are used by a number of consuming entities, such as payors 206 and healthcare providing (or provider) organizations 226, that contract with or employ the healthcare professionals. In addition, malpractice insurance providers 224 may serve as consuming entities of a variety of data for a number of purposes, such as determining policy premiums.

Healthcare providing organizations 226 include hospitals, clinics, physician offices, and generally any entity contracting with or employing a healthcare professional to provide care. These organizations may serve as the PSPs of a wide variety of quality indicators, such as treatments provided, treatment outcomes, procedures provided, procedure outcomes, roles performed, competencies, privileges gained/lost, employment/contract status, and hours worked. Because healthcare providing organizations 226 make employment and contracting decisions and have regulatory compliance requirements, these organizations may also serve as consuming entities for a wide variety of healthcare personnel data. Before a healthcare providing organization 226 can hire or contract with a healthcare professional on a permanent or temporary basis, it must obtain almost all of the information provided by each of the PSPs.

A number of national comparative databases 228 examine quality indicators from healthcare providing organizations. Generally, a healthcare providing organization may manually submit data, such as patient treatment and outcomes, to such a comparative database. The database maintains data submitted from multiple organizations and compares the submitting healthcare organization data with information supplied by other organizations to determine how the submitting organization is performing. Information contained in the comparative databases 228 may be captured by and maintained in the personnel profile manager 202.

The information provided by the PSPs is captured by the personnel profile manager 202, which maintains a database 230 for storage of the data. The database 230 maintains a profile for each healthcare professional. Each piece of data is associated with a healthcare professional profile and stored with that profile in the database 230.

Figure 3:
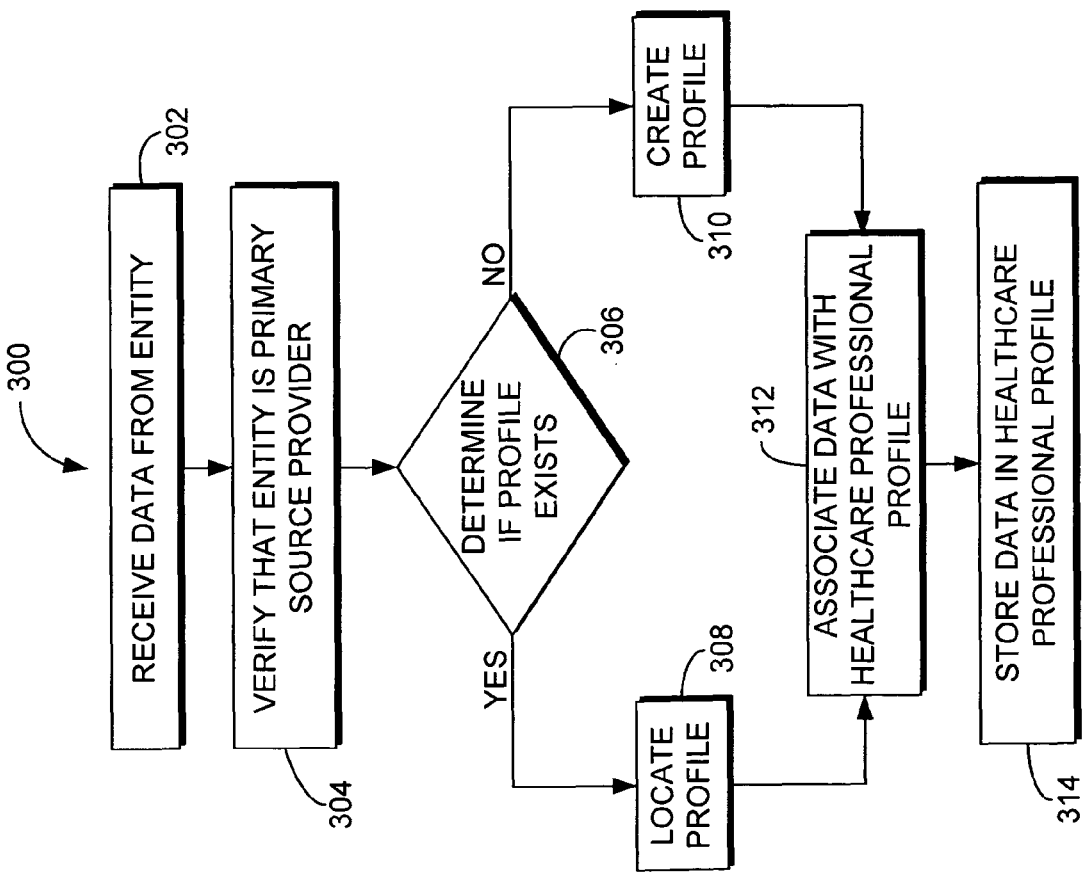
FIG. 3 is a flow diagram of a method for receiving information regarding healthcare personnel in accordance with an embodiment of the present invention.

Turning to FIG. 3, a flow diagram of an exemplary embodiment of the invention is illustrated which shows a method 300 through which the personnel profile manager acquires and maintains healthcare personnel data from PSPs. The process begins at step 302 when the personnel profile manager receives data from an entity. The data submission may have been prompted by a request for data from the personnel profile manager. Alternatively, the entity may submit the healthcare personnel data without such a request.

At step 304, the personnel profile manager verifies that the submitting entity is an authorized PSP for the data provided. The system provides logic to determine which organization is the PSP for each piece of data and enables only that organization to contribute or edit the data. For example, only accredited education providers may be enabled to provide and edit data regarding degrees earned by healthcare professionals. Other entities, such as payors or healthcare professionals themselves, may not be permitted to submit or change this piece of information. The purpose of this verification step is to ensure that accurate data are maintained by the personnel profile manager and to prevent opportunities for fraud or misrepresentation.

After verifying that the submitting entity is an authorized PSP for the data submitted, the personnel profile manager associates the submitted data with appropriate individual healthcare professionals. Data may be submitted simultaneously for multiple healthcare professionals. Thus, each piece of data must be separated and associated with its respective healthcare professional. For example, an accredited education provider may submit degree information for all its graduates upon graduation. The personnel profile manager separates the degree information for association with each individual healthcare professional. At step 306, the personnel profile manager determines whether a profile exists for each healthcare professional for which data were submitted. If a profile exists for a particular healthcare professional, the personnel profile manager locates the profile, as shown at step 308. If no profile exists for a particular healthcare professional, the personnel profile manager creates a profile for the professional, as shown at step 310.

After locating or creating the required healthcare professional profile, the personnel profile manager associates each piece of the submitted data with the appropriate profile, as shown at step 312. Association of data with a profile for a healthcare professional may be accomplished by using any method for identifying the healthcare professional. By way of example and not limitation, a healthcare professional may be identified using a social security number, a license number, a DEA number, or a new unique identification code established for the personnel profile manager.

Once the data have been associated with the appropriate profile, the personnel profile manager populates the profile with the submitted data, as shown at step 314. If the profile already contains data corresponding with the piece of information that was submitted, the personnel profile manager can treat the new data and existing data in a number of ways. First, the existing data may be maintained with the new data. Second, the existing data may be replaced with the new data. Finally, the existing data may be maintained and the new data may be rejected.

Figure 4:
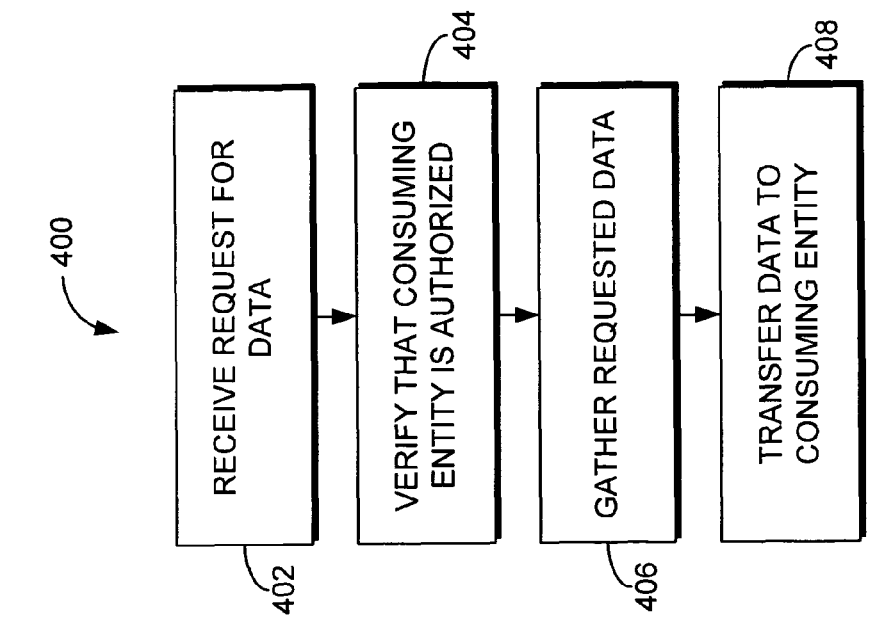
FIG. 4 is a flow diagram of a method for distributing information regarding healthcare personnel in accordance with an embodiment of the present invention.

Healthcare personnel data that has been collected by the personnel profile manager may be requested by and transferred to consuming entities. FIG. 4 illustrates a flow diagram of an exemplary embodiment of the invention, which shows a method 400 for distributing healthcare personnel data. The process begins at step 402 when the personnel profile manager receives a request for data. The request may be a one-time request for information from a consuming entity. Alternatively, a consuming entity may desire to be periodically updated with personnel profile data. Thus, the request may be an automatic process based on the consuming entity's need for data updates.

At step 404, the personnel profile manager verifies that the consuming entity is authorized to obtain the requested data. Because the personnel profile manager contains a wide range of personnel data, there may be privacy and security concerns with the dissemination of the information. In addition, the personnel profile manager may be a subscription service, whereby only paying subscribers may consume data. Thus, the system must verify that the consuming entity is authorized to receive the requested data. Some consuming entities may be authorized to obtain only certain pieces of information. Thus, the personnel profile manager will compare the requested data with the entity's authorizations to verify the request.

If the consuming entity is authorized to receive the requested data, the personnel profile manager gathers the information, as shown at step 406. The request may be for data associated with certain identified healthcare professionals. Alternatively, the request may be for data associated with all healthcare professionals that the consuming entity has a relationship with. For example, a healthcare providing organization may request data for a single physician, several identified physicians, or all healthcare professionals employed by or contracted with the healthcare providing organization. In addition, the consuming entity may request either certain pieces or all data for each healthcare professional. Thus, the personnel profile manager determines from the request the healthcare professionals indicated and the pieces of information required. The personnel profile manager then accesses its database and pulls the information from the profile for each healthcare professional. If the requested information is not stored in the healthcare professional's profile or if the data stored in the profile is not current, the personnel profile manager may request the data from the appropriate PSP. Finally, at step 408, the personnel profile manager transfers the data to the consuming entity.

Because the personnel profile manager includes a wide variety of information, it provides the capability to analyze the data to determine variances in performance at the individual healthcare professional level. These variances in performance can be used for purposes such as protecting patients from potentially harmful situations by providing alerts when certain performance variances occur. Thus, in an embodiment of the invention, the system provides variance alerts to consuming entities.

Figure 5:
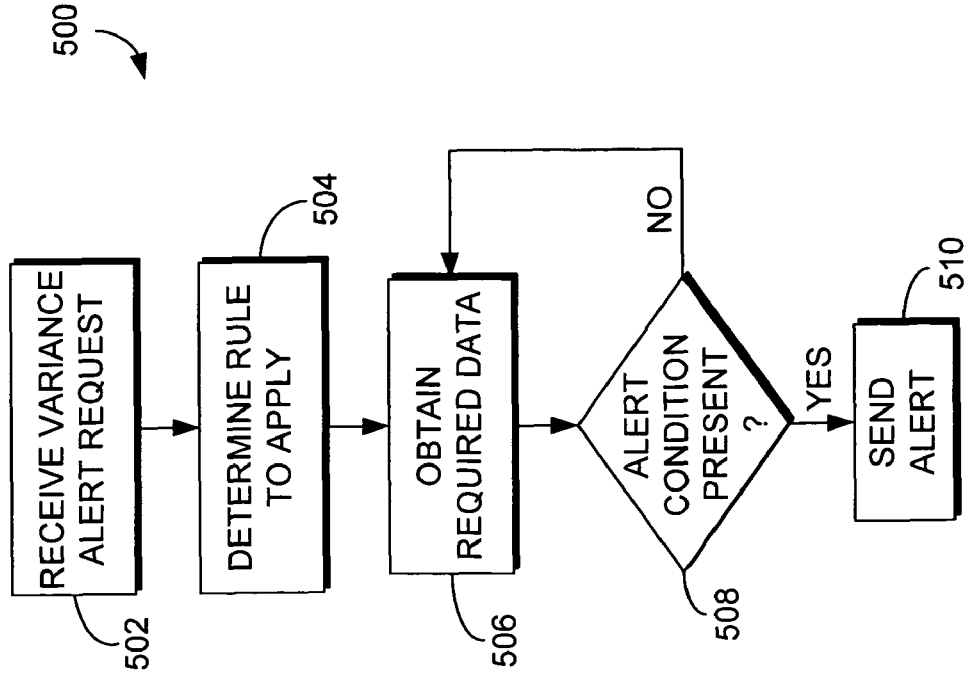
FIG. 5 is a flow diagram of a method for providing variance alerts in accordance with an embodiment of the present invention.

Referring to FIG. 5, a flow diagram of an exemplary embodiment of the invention is illustrated which shows a method 500 for providing a variance alert. The process begins at step 502 when the personnel profile manager receives a request for a variance alert. The request may be for a one-time alert, wherein the current data are checked for the particular variance condition requested. Alternatively, the request may be for an automatic alert if the particular variance condition ever occurs.

At step 504, the rule to apply for the variance alert is determined. The rule defines the condition that, if met, triggers the variance alert. By way of example and not limitation, a rule may be based on a healthcare professional's credentials (e.g., absence of a certification), procedure/treatment outcomes, or volume of procedures/treatments. A rule may be based on the number of patient deaths or the number of places employed for a given period of time. A rule may be based on a best practice guideline from a medical authority or on a comparative analysis of the healthcare professional's data with data from similarly situated healthcare professionals. Generally, any type of rule may be established by a consuming entity and used for a variance alert. The rule may incorporate severity and risk adjustment tools that are known in the art (e.g., the All-Patient Refined Diagnosis Related Groups system) to accommodate for variations in different practice areas. For example, a physician working in an intensive care unit can be expected to experience more patient deaths than a general practitioner.

The data required to determine if the alert condition is present are obtained from the database at step 506. The personnel profile manager determines what data are required based on the rule established in the previous step. The manager then determines if the required data are available and current in the healthcare professional's profile. If the information is not available or is not current, the personnel profile manager may request the data from the appropriate PSP or may return an error message indicating the absence of data necessary to provide a variance alert.

If the required data are available and current, the personnel profile manager will pull the information from the healthcare professional's profile and determine whether an alert condition is present, as shown at step 508. The personnel profile manager will compare the data with the rule established in step 504 to determine if the rule has been violated.

As shown at step 510, if the personnel profile manager determines that an alert condition is present, it will send a variance alert to the consuming entity that requested the alert. Alternatively, if the alert condition is not present at step 508, the personnel profile manager may periodically recheck the data contained in its database to determine if the variance condition has occurred. Because the personnel profile manager is continuously updated with new healthcare personnel data, the alert condition may occur at another time.

As a specific example of a volume-based variance alert, a hospital may wish to monitor surgeons it provides privileges to perform coronary artery bypass graft (CABG) surgeries. The hospital may set a rule based on the guideline from the American College of Cardiology/American Heart Association, which indicates that mortality after CABGs is higher for surgeons who perform less than 100 cases on an annual basis. Thus, a rule may be established to provide a variance alert if a particular surgeon's number of CABG surgeries is less than 100 per year. Once this rule is set, the personnel profile manager will periodically check data for each of the surgeons indicated by the hospital and alert the hospital if any of the surgeons has cases fewer than the set number.

As a specific example of a quality outcome-based variance alert, a hospital may wish to monitor physicians providing treatment to patients admitted with acute myocardial infarction (AMI). A rule may be based on the guideline that patients admitted with AMI who do not have contraindications should receive aspirin within 24 hours before or after arrival at the hospital. Thus, a rule may be established to provide a variance alert if the percentage of all AMI patients treated by a physician with aspirin within the first 24 hours of hospital arrival is lower than 95%. Once this rule is set, the personnel profile manager will periodically check data for each of the physicians indicated by the hospital and alert the hospital if a physician's percentage falls below the percentage set by the rule for the alert.

Figure 6:
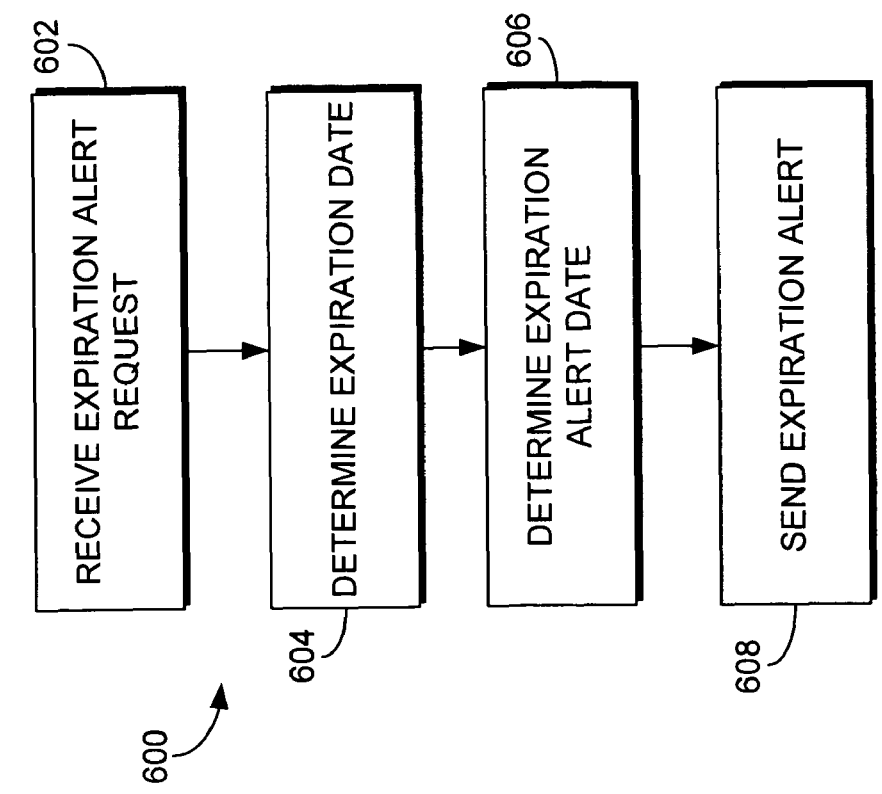
FIG. 6 is a flow diagram of a method for providing expiration alerts in accordance with an embodiment of the present invention.

Healthcare professionals' credentials, such as licenses, certifications, mandated training, formal education, and vaccinations, are often time-limited such that they expire after a certain period of time. Another embodiment of the invention provides alerts for expiration of such credentials. FIG. 6 illustrates an exemplary embodiment of the invention, which shows a method 600 for providing an expiration alert. The process begins at step 602 when the personnel profile manager receives a request for an expiration alert. The request consists of an initial set-up for the alert condition by specifying a number of items. First, the healthcare professional that an expiration alert is desired for must be identified. Next, the type of credentials for which an expiration alert is requested must be indicated. For example, the alert may be requested for the expiration of a license or a certification. Finally, the timing of the alert condition must be specified. For example, the entity requesting the alert may specify that the alert should occur a month before the expiration date. In addition, multiple alerts with different times may be established for a single expiration event. For example, the entity may specify that alerts should occur a month before, a week before, and the day of the expiration.

At step 604, the expiration date is determined based on the request. The personnel profile manager determines the healthcare professional identified by the request and accesses the profile of that professional. The personnel profile manager then determines whether the profile contains current information regarding the expiration date for the credential specified by the request. If data are not contained in the profile or if the data are not current, the personnel profile manager may request the information from the appropriate PSP or may provide an error message to alert the requestor that the data required for the alert is not available in the database.

If the expiration data are available, the personnel profile manager next determines the alert date, as shown at step 606. The alert date is established using the timing indicated by the alert request and the expiration data contained in the database. For example, if the alert is requested for a month before the expiration date and the expiration date is indicated as March 25, the alert date will be set at February 25. Finally, at step 608, the alert is automatically sent by the personnel profile manager to the requesting entity at the set alert date.

Figure 7:
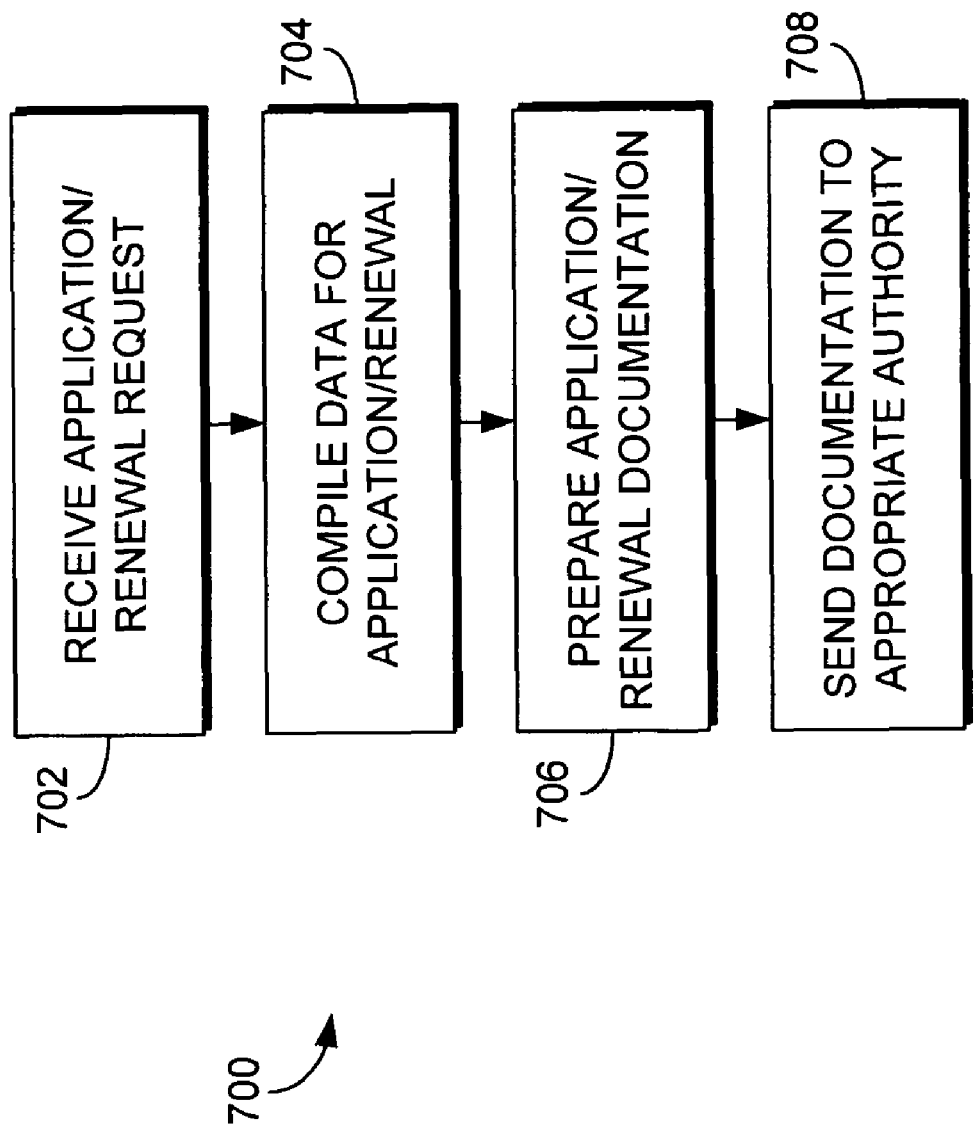
FIG. 7 is a flow diagram of a method for providing application and renewal services via the personnel profile manager in accordance with an embodiment of the present invention.

In a further embodiment of the invention, the personal profile manager provides the capability to gather data for the purpose of applying for or renewing certain credentials, such as licenses and certifications. FIG. 7 illustrates an exemplary embodiment of the invention showing a method 700 for providing application and renewal services via the personnel profile manager. The process begins at step 702 when the personnel profile manager receives a request to gather data for an application or a renewal. The request may be submitted by the healthcare professional or may be submitted on behalf of the healthcare professional by his/her employer (i.e. a healthcare providing organization). The system could also be configured such that the authority administering the credentials (e.g., a state licensing board) may request the necessary data from the personnel profile manager. For renewals, the process may also be tied into an expiration alert such that an expiration alert and renewal could be requested simultaneously.

At step 704, the personnel profile manager compiles the data required for the application or renewal. The personnel profile manager determines what information is required for the requested application or renewal and then pulls the data from the healthcare professional's profile. If additional data are required that is not available in the database or if updated data are required, the personnel profile manager may request the data from the appropriate PSPs.

At step 706, the required documentation for the application or renewal is prepared using the compiled data. Once the documentation has been prepared, it is submitted electronically to the authority administering the credentials, as shown at step 708. Alternatively, the authority may not require any documentation to be submitted, and the application or renewal may be accomplished by a data push from the personnel profile manager to the authority. In other words, the personnel profile manager compiles the required data and transfers it to the authority without preparing any documentation.

For example, the Kansas State Board of Nursing requires continuing education hours to be met prior to allowing the renewal of a nursing license. Other states have similar nursing license renewal requirements. Since the training records for nurses participating in accredited continuing education courses are kept by the education provider, the education provider could act as a PSP by posting the education courses and related hours taken by nurses to the personnel profile manager. The renewal form for the nursing license then could be filled out using the continuation education course data and any other necessary data from the personnel profile manager.

The present invention has been described in relation to particular embodiments, which are intended in all respects to be illustrative rather than restrictive. Alternative embodiments will become apparent to those of ordinary skill in the art to which the present invention pertains without departing from its scope. Substitutions may be made and equivalents employed herein without departing from the scope of the invention as recited in the claims. For example, additional steps may be added and steps omitted without departing from the scope of the invention. It will be understood that certain features and subcombinations are of utility and may be employed without reference to other features and subcombinations. This is contemplated and within the scope of the claims.

The invention claimed is:

1. One or more tangible computer storage media having stored thereon computer-readable instructions that, when executed, cause a computing device to perform a method for managing healthcare personnel data elements of a healthcare professional, the method comprising:

receiving from a patient a service rating that describes a quality of services provided by the healthcare professional;

receiving from a healthcare providing organization a description of outcomes of procedures that were performed by the healthcare professional;

receiving payor-plan membership information that includes a payor-insurance plan of which the healthcare professional is a member;

receiving association information that includes a professional-association certification achieved by the healthcare professional and that includes a professional-association membership held by the healthcare professional;

receiving education information that includes a degree earned by the healthcare professional;

receiving licensing information that includes a state licensee obtained by the healthcare professional;

receiving malpractice information that identifies a malpractice-insurance policy of the healthcare professional;

associating the service rating that was received, the payor-plan membership information, the association information, the education information, the licensing information, the malpractice information, and the description of outcomes with a profile of the healthcare professional, wherein the profile is a repository of a plurality of healthcare personnel data elements of the healthcare professional that is continuously updated with current healthcare personnel data elements; and storing the received service rating, the payor-plan membership information, the association information, the education information, the licensing information, the malpractice information, and the description of outcomes.

2. The one or more tangible computer storage media of claim 1, wherein the method further comprises receiving from a continuing education provider an identification of continuing education courses completed by the healthcare professional and storing the received identification of continuing education courses in the profile.

3. The one or more tangible computer storage media of claim 1, further comprising:
creating a profile for the healthcare professional.

4. The one or more tangible computer storage media of claim 1, further comprising:
receiving an update to the at least one of the service rating and description of outcomes.

5. The one or more tangible computer storage media of claim 1, further comprising:
verifying the accuracy of at least one of the service rating and description of outcomes.

6. The one or more tangible computer storage media of claim 1, further comprising:
sending to at least one of the patient and the healthcare providing organization a request to submit at least one healthcare personnel data element of the healthcare professional, wherein the request is sent via a network.

7. The one or more tangible computer storage media of claim 1, wherein the healthcare professional is a physician, a physician assistant, a nurse, other credentialed healthcare professional, or a combination thereof.

8. The one or more tangible computer storage media of claim 1, further comprising:
receiving from a consuming entity a request to receive at least one healthcare personnel data element of the healthcare professional.

9. The one or more tangible computer storage media of claim 8, further comprising:

verifying that the consuming entity is authorized to receive the requested at least one healthcare personnel data element.

10. The one or more tangible computer storage media of claim 8, further comprising:

sending the requested at least one healthcare personnel data element to the consuming entity.

11. The one or more tangible computer storage media of claim 8, wherein the consuming entity is a healthcare professional, a patient, a peer, a payor, the Drug Enforcement Administration, a professional association, an accredited education provider, the American Medical Association, a state licensing board, the National Practitioner Data Bank, the Healthcare Integrity and Protection Data Bank, a continuing education provider, a malpractice insurance provider, a healthcare providing organization, a comparative database, or a combination thereof.

12. One or more tangible computer storage media having computer readable instructions stored thereon that, when executed, cause a computing device to perform a method for managing healthcare personnel data of a healthcare professional, the method comprising:

receiving payor-plan membership information that includes a payor-insurance plan of which the healthcare professional is a member;

receiving association information that includes a professional-association certification achieved by the healthcare professional and that includes a professional-association membership held by the healthcare professional;

receiving education information that identifies a degree earned by the healthcare professional;

receiving licensing information that identifies a state licensee obtained by the healthcare professional;

receiving malpractice information that identifies a malpractice-insurance policy of the healthcare professional;

receiving from a healthcare providing organization a set of quality indicators that includes one or more of treatments provided at the healthcare providing organization, treatment outcomes experienced at the healthcare providing organization, procedures provided at the healthcare providing organization, and procedure outcomes experienced at the healthcare providing organization;

associating by the computing device the payor-plan membership information, the association information, the education information, the licensing information, the malpractice information, and the set of quality indicators with a profile of the healthcare providing organization;

providing by the computer device the set of quality indicators to a comparative database, which compares the set of quality indicators to another set of quality indicators of another healthcare providing organization;

receiving from the comparative database a comparison of the set of quality indicators to the other set of quality indicators, wherein the comparison indicates how the healthcare providing organization is performing; and storing by the computer device the comparison in the profile.

* * * * *